United States Patent [19]

Gerbaulet et al.

[11] Patent Number: 4,924,389
[45] Date of Patent: May 8, 1990

[54] DEVICE FOR IMPLEMENTING A METHOD FOR FEEDING PERSONS

[76] Inventors: Claude Gerbaulet, 15, rue de la Touviere, 75400 Evian-les-Bains; Sonia Ferry, 204, rue de la Croix Nivert, 75015 Paris, both of France

[21] Appl. No.: 194,989
[22] PCT Filed: Aug. 28, 1987
[86] PCT No.: PCT/FR87/00335
 § 371 Date: May 2, 1988
 § 102(e) Date: May 2, 1988
[87] PCT Pub. No.: WO88/01770
 PCT Pub. Date: Mar. 10, 1988

[30] Foreign Application Priority Data

Sep. 1, 1986 [FR] France ................. 86 12274

[51] Int. Cl.$^5$ ............................................. G06F 15/42
[52] U.S. Cl. ................................................ 364/413.29
[58] Field of Search ............... 364/413.29, 709.03, 364/715.05

[56] References Cited

U.S. PATENT DOCUMENTS

| | | | |
|---|---|---|---|
| 4,192,000 | 3/1980 | Lipsey | 364/413.29 |
| 4,321,674 | 3/1982 | Kramer et al. | 364/413.29 |
| 4,575,804 | 3/1986 | Ratcliff | 364/715 |
| 4,686,624 | 8/1987 | Blum et al. | 364/413.29 |
| 4,796,182 | 1/1989 | Duboff | 364/413.29 |

FOREIGN PATENT DOCUMENTS

| | | |
|---|---|---|
| 59-33570 | 2/1984 | Japan . |
| 0433502 | 6/1974 | U.S.S.R. . |
| 8602194 | 4/1986 | World Int. Prop. O. . |

OTHER PUBLICATIONS

"Electronic Diet Controller", K. Moran, Computer Design, Aug. 1977, pp. 116-118.
"Improving Diet, Byte by Byte", S. Squies, Washington Post, Jan. 30, 1985.
"Mayo Clinic Diet Manual", Copyright 1971, pp. 71, 72, 132, 160.

Primary Examiner—Jerry Smith
Assistant Examiner—Steven G. Kibby
Attorney, Agent, or Firm—Browdy and Neimark

[57] ABSTRACT

A first memory stores a calorie goal and quantities of food in several categories which a person anticipates will be consumed during a predetermined day. The quantity of food eaten during the preceding days are stored in a second memory. A computer determines the recommended number of calories and quantities of food in each category for the predetermined day as a function of the quantities consumed during the preceding days. The recommended quantities are stored in a third memory and comparisons are made between the estimated quantities and the recommended quantities, the results of which are displayed. The device, used with or without scales, provides for a healthy and balanced nutrition.

11 Claims, 5 Drawing Sheets

FIG_1

FIG_2

FIG. 3

FIG_4

FIG_5

DEVICE FOR IMPLEMENTING A METHOD FOR FEEDING PERSONS

BACKGROUND OF THE INVENTION

This invention relates to a device for implementing a method for feeding persons, in which method the recommended energy ration, for a given day, to a given person, is dependent upon the energy rations consumed by said person during the preceding day.

The inventive device allows then one to remain in good health thanks to a sound diet, balanced and adapted to one's morphology, and, in some cases, to follow a thinning or fattening diet.

To implement the feeding methods of the above-defined type, which have generally been elaborated by dieteticians, food scales can be found on the market that allow, on the one hand and in a conventional manner, to know the weight of the amount of food put down on the pan, and on the other hand to know the energy supply contributed by this amount of food.

Such a scale includes a mechanical-electrical module delivering an electric signal representative of the weight of the amount of food put down on the pan, and an electronic module capable of converting this signal so that it becomes representative of this amount of food's energy value. As is known, food can be subdivided into a number of categories, the food in one category having essentially the same energy value per mass unit. Taking care of only putting down at the same time on the pan food belonging to the same category, and controlling the electronic module so that it makes the conversion in grams in energy units (Kjoule, Kcalorie commonly called Calorie or Cal.) corresponding to that category, one obtains the energy value of the food.

But such a global evaluation proves inadequate for a good diet hygiene for it does not take into account the balance in the food's composition, nor the fact that the effects of overfeeding the human body differ according to the foods. This latter point is naturally particularly important when one has to recommend a food ration for a given day as a function of the food rations having been consumed during the preceding days.

The object of this invention is to obviate these drawbacks.

SUMMARY OF THE INVENTION

To this effect it relates to a device for implementing a method for feeding persons in which, the food being subdivided into a fixed number of categories the energy ration recommended for a given day and for each category to a given person depends on the rations consumed by said person during the preceding days in said category, this device being characterized in that it includes:

a first memory means to memorize each quantity, as anticipated by said person, of food belonging to each of said categories for his/her diet during that day, a second memory means connected to the outlet of said first memory means, to memorize each quantity, as consumed by said person, of food belonging to each of said categories during at least one of said preceding days.

a first computer means connected to the outlet of said second memory means to determine each quantity of food in each of said categories which is recommended for said person, as well as said energy ration recommended to said person for his/her diet during said day, a third memory means, connected to the outlet of said first computer means, to memorize said recommended quantities and said recommended energy ration, a second computer means, connected to the outlet of said first memory means, to determine the energy ration anticipated by said person for his/her diet during said day, a first comparison means connected to the outlet of said first memory means, to the outlet of said second computer means and to the outlet of said third memory means, to compare each of said anticipated quantities to each said recommended quantity in the same category, and to compare said anticipated energy ration to said recommended energy ration, a first indicator means, controlled by the outlet of said first comparison means, and controlling means for writing, in said second memory means, said anticipated and consumed quantities and then writing, in said third memory means, new recommended quantities of food in each of said categories, and the new recommended energy ration for the next day.

Thanks to the inventive device one can compare in a simple and instant way quantities of food whose consumption is anticipated during said day in each of said categories, to the recommended quantities of food depending on quantities consumed during preceding days.

In the case where anticipated quantities differ from recommended quantities, one can either change anticipated quantities to bring them in agreement with recommended quantities for the next day, which allows thus one to respect the balance of each category over a period of several days.

As food is generally consumed during the days in several meals each including several courses, the inventive device includes moreover, in an advantageous embodiment, a fourth memory means to memorize each anticipated quantity, per course in the next meal, of food from each of said categories, a summing up means, connected to the outlet of said fourth memory means to sum up said anticipated quantities, per course, of food from the same category, and thus deliver anticipated quantities, for said next meal, of food from each of said categories, and a fifth memory means connected to the outlet of said summing up means to memorize each consumed quantity during all past meals of said day, of food from each of said categories, and connected to the inlet of said first memory means.

The use of the inventive device is made easier by the fact that food quantities are then memorized course by course during preparation of the meals, which allows one to knowingly correct their composition if need be.

According to another advantageous feature, the inventive device includes moreover, a monitoring means connected to the outlet of said summing up means and to the outlet of said third memory means, to monitor the composition of said next meal, and a second indicator means, controlled by said monitoring means.

The latter includes, in an advantageous embodiment, a third computing means, connected to the outlet of said summing up means, to determine the energy value of said next meal, a fourth computing means connected to the outlet of said third memory means to determine a given fraction of said recommended energy ration, and a second comparison means, connected to the outlet of said third computing means and to the outlet of said fourth computing means for comparing said energy value with said fraction and controlling said second indicator means when said energy value is superior to said fraction.

According to another advantageous feature of the inventive device said first computing means includes.

a sixth memory means for said person's morphological data, a fifth computing means, connected to the outlet of said sixth memory means, to determine the daily energy ration adapted to said morphological data, a sixth computing means, connected to the outlet of said fifth computing means, to determine each daily quantity, as adapted to said morphological data, of food to be consumed in each category, a seventh computing means, connected to the outlet of said sixth computing means, and to the outlet of said second memory means, to determine each said recommended quantity and said recommended energy ration, and said seventh computing means are arranged so as to determine each said recommended quantity of food from each of said categories as a function, on the one hand, of said adapted daily quantity of this food, and on the other hand, of the quantity of this food consumed during said preceding days, taken in all the greater number since this food must absolutely be taken every day.

Other features and advantages of the invention will appear in the following description of different embodiments of the inventive device, made by reference to the appended drawings.

DESCRIPTION OF THE PREFERRED EMBODIMENTS

The device we shall now describe, as an example, referring to FIG. 1-4, includes here a pair of scales with which the user of the device weighs the quantities of food he expects to consume. The scales give, in this case as an electric signal, representative data for the mass of weighted food. The device includes moreover, as will be seen later, electronic memory, computing and display circuits, arranged so as to allow the user to monitor and see whether his/her food is healthy, balanced and adapted to his/her morphology, and perhaps to follow a thinning, fattening or balance-restoring diet.

In order to simplify the drawings and their understanding, mass connections and feeding connections of the diverse blocks are not represented in the drawings. Other connections are represented with a single line, then symbolizing:

either a connection comprising one conducting wire used for transmitting an analog signal, or a binary signal, or data taking the form of a 'series' type digital signal, or a connection comprising several parallel conducting wires used for transmitting data as a 'parallel' type digital signal.

Nine categories of food are here taken into account. In Table I is briefly indicated the definition of each of these categories, the symbolic abbreviation associated therewith along this description, and the approximate energy value of one hundred grams (0.2205 lb) of this food (the mass unit thereafter used for weighing food is the gram).

TABLE I

| Category | Abbreviation | Energy value/100 g |
|---|---|---|
| Green vegetables | LV | 40 cal |
| Fresh fruit | FR | 50 cal |
| Cereals. Starch. Bread | FC | 300 cal |
| Meat. Fish. Eggs | VP | 160 cal |
| Dairy foods. soft white cheese | LA | 80 cal .../... |
| Dry cheese | FM | 250 cal |
| Butter, Oil, Margarine | BH | 600 cal |
| Sugar. Jam & Marmelade. | SU | 400 cal |
| Honey Wine. Beer | ALC | 70 cal |

Naturally the above categories and corresponding energy values are only given as exemplary and one can naturally choose a smaller or, on the contrary, a higher number of categories, or define categories from other nutritional criteria than those used in the above example. Moreover, food categories of an equivalent nutritional quality can be put together under one category (meat/fish/eggs in the above example) or divided into distinct categories (green vegetables/fresh fruit, or dairy foods, soft white cheese/dry cheese in the above example) for display reasons... These distinct categories can be coupled for processing and for the apparatus' specifications.

Figure 1:
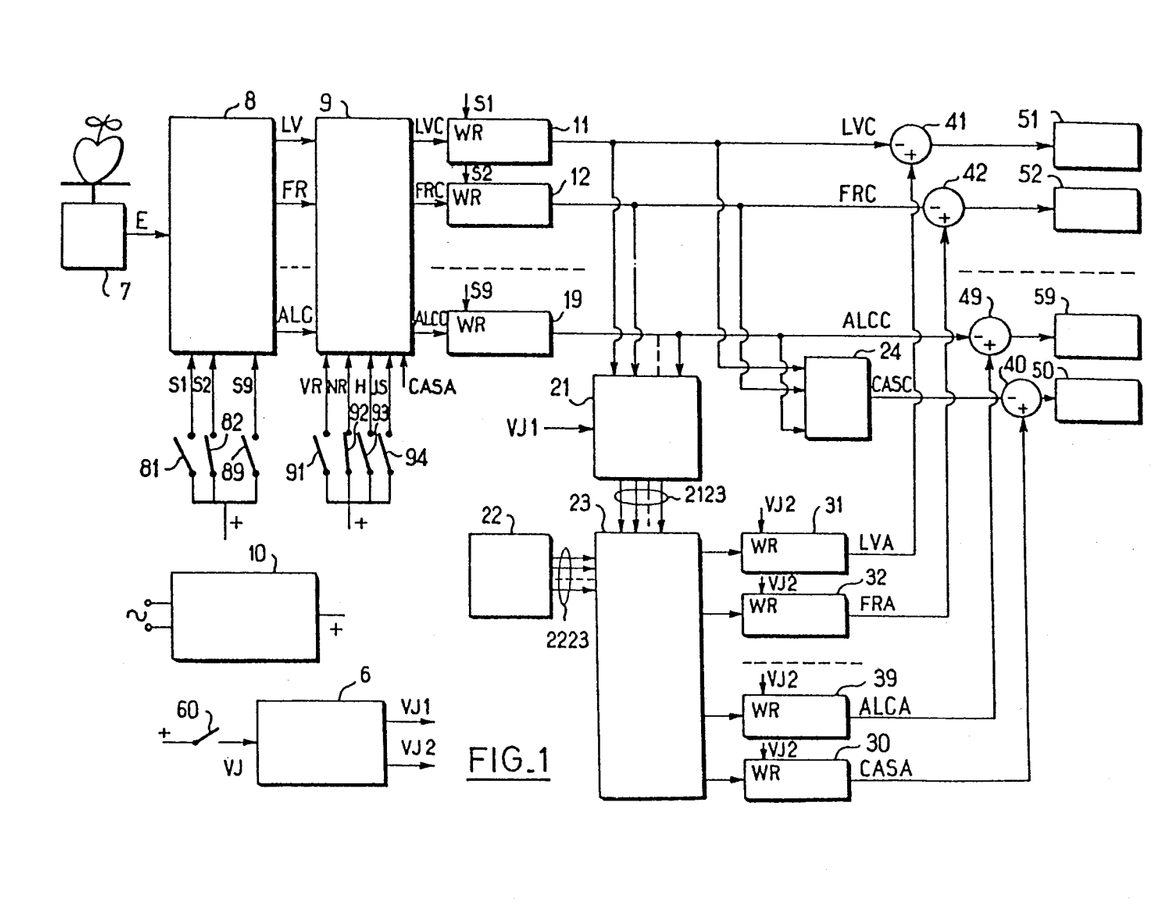
FIG. 1 is a block diagram of the inventive device.

Referring now to FIG. 1, the scale 7, marketed here by The TERRAILLON Company (SCAIME gauges), Reference 5PZ, delivers at its outlet a digital signal E representative of the weight and therefore of the amount of food put down on its pan.

A multiplexer 8 is provided with an inlet receiving the digital signal E, as many outlets as the different food categories, nine in this case, delivering digital signal LV, FR, ... ALC, and nine control inlets receiving nine binary signals S1–S9.

The binary signals, S1–S9, are produced by way of nine switches, 81–89, connected at one end to a voltage corresponding to the high logic level, which voltage is produced by a feeding circuit of known type, 10, connected to an electric energy source, which is either a cell, a reloadable battery or supply circuit, which is also used to feed all the device's circuits, in a conventional, therefore not shown, manner as already mentioned.

Multiplexer 8, of known type, is arranged to connect the inlet receiving signal E to the outlet delivering signal LV when signal S1 is at high level, to the outlet delivering signal FR when signal S2 is at high level, etcetera...

A circuit 9 for composing and commanding meals, which will be described in greater detail below, is here provided with nine inlets receiving signal LV, FR, ... ALC, nine outlets delivering digital signal LVC, FRC ... ALCC, four control inlets receiving four binary signals VR, NR, H and JS, and a tenth inlet receiving a digital signal CASA.

Binary signals VR, NR, H and JS are produced by way of four switches, 91-94, connected at one end to the tension corresponding to high logic level.

Nine memory-registers, 11-19, of known type, are each provided with an inlet receiving signals LVC, FRC, . . . ALCC, respectively, an outlet delivering these same digital signals LVC, FRC, . . . ALCC, respectively, and a writing control inlet receiving signals S1, S2, . . . S9, respectively.

A memory circuit, 21, for amounts consumed during preceding days, which will be described in greater detail later, is provided with nine inlets receiving signals LVC, FRC, . . . , ALCC, a plurality of outlets united in a bundle, 2123, and a writing control inlet receiving a binary signal, VJ1.

A computing circuit, 24, is provided with nine inlets receiving signals LVC, FRC, . . . , ALCC, and an outlet delivering a digital signal, CASC. The computing circuit, 24, is arranged to multiply the signal which is present on each inlet by a given coefficient and to add the nine products thus obtained. As an example, circuit 24 computes here:

$$CASC = 0.4LVC + 0.5FRC + 3FCC + 1.6VPC + 0.8LAC + 2.5FMC + 6BHC + 4SUC + 0.7ALCC.$$

Circuit 24 is thus within reach of a man of the art and will not be further described.

Ten subtracters, 40-49, of known type, are each provided with a minus inlet receiving signals CASC, LVC, FRC, . . . ALCC, respectively, a plus inlet receiving numerical signals CASA, LVA, FRA, . . . ALCA, respectively, and an outlet delivering a digital signal.

Ten indicators, 50-59, are each connected to the outlet of the ten subtracters, 40-49, respectively. Each indicator includes here an alphanumeric display device of known type, for displaying the numerical value of the signal which is present at its inlet.

A memory circuit 22 for the user's morphological data, of known type, is here provided with a plurality of outlets, united in a bundle, 2223, each delivering a digital signal representative of the user's morphology.

By way of example, these signals add up to five in this case, and include:
signal T representing height
signal NS representing sex
signal PR representing weight
signal VO representing the user's general morphology, longilineal, intermediate or brevilineal
signal F representing the user's physical activity, slight, average or intense.

Still as an example, the numerical values memorized in memory circuit 22 are given in Table II.

TABLE II

| T | height in centimeters |
|---|---|
| NS | 4 for a man |
| | 2 for a woman |
| PR | weight in kilograms |
| VO | 1 longilineal morphology |
| | 1.05 intermediate morphology |
| | 1.10 brevilineal morphology |
| F | 1 slight physical activity (sedentary) |
| | 2 average physical activity |
| | 3 intense physical activity |

A computing circuit, 23, which will be described in greater detail later, is provided with a first plurality of inlets connected to bundle 2223, a second plurality of inlets connected to bundle 2123 and ten outlets each delivering a numerical signal.

Ten memory-registers, 30-39, of known type, are each provided with an inlet connected to each of the ten outlets of the computing circuit 23, an outlet delivering the numerical signals CASA, LVA, . . . , ALCA, respectively, and a writing control inlet receiving a binary signal, VJ2.

An electronic circuit, 6, for writing control, is provided with an entrance receiving a binary signal, VJ, produced by way of a switch, 60, connected at one end to the voltage corresponding to high logic level, and two outlets delivering binary signals VJ1 and VJ2. The electronic circuit, 6, is arranged so that, when signal VJ comes to high level, the binary signals VJ1 and VJ2 control writing in memory 21 and in registers 30-39, respectively, writing in registers 30-39 being slightly delayed in relation to writing in memory 21. Circuit 6 is therefore within reach of the specialist and will not be further described.

Figure 2:
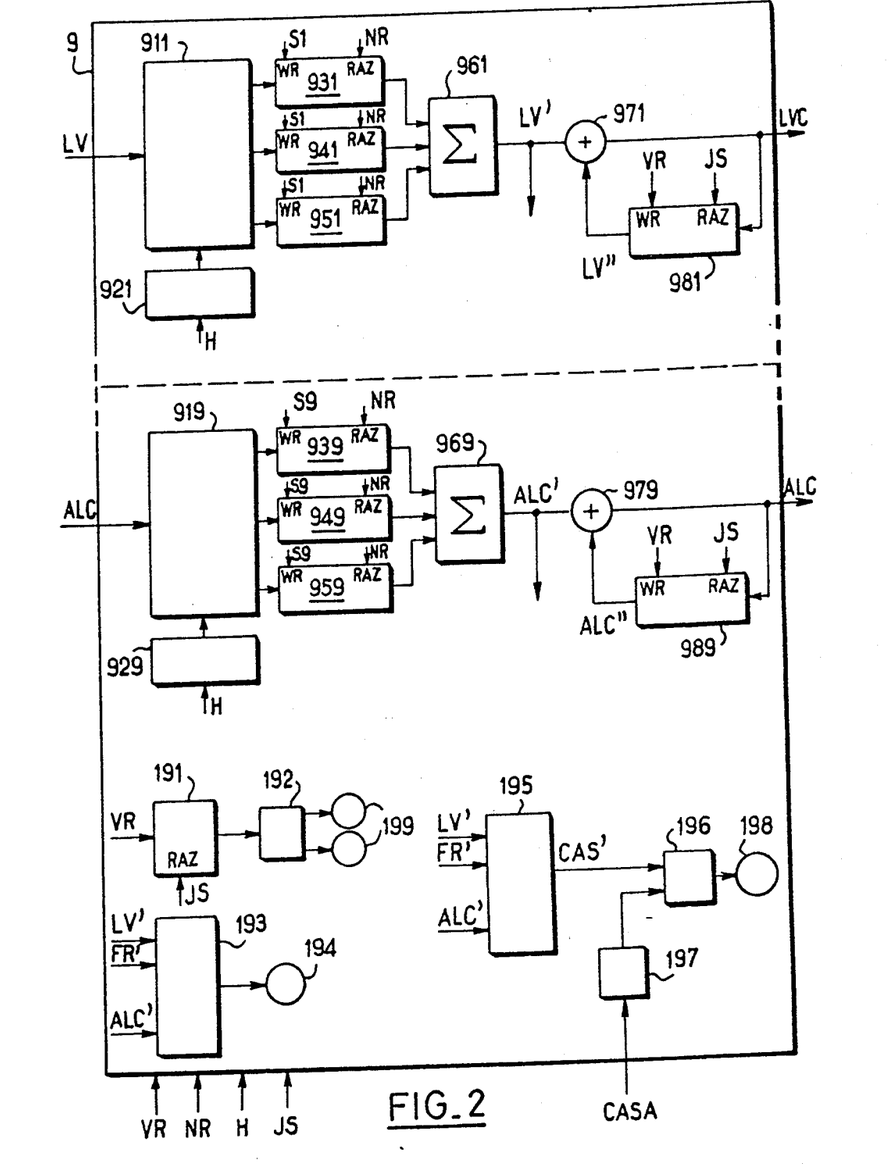
FIG. 2 is a block diagram of the circuit for making up and monitoring meals, which circuit is a part of the device of FIG. 1.

Referring to FIG. 2, circuit 9 for composition and control of meals is now described. This circuit includes first nine identical paths, connecting the nine inputs receiving signals LV, FR, . . . ALC to the nine outlets delivering signals LVC, FRC, . . . ALCC, respectively. In order not to encumber the Figure, only paths for processing signals LV and ALC are represented.

The path for processing signal LV includes a multiplexer, 911, of known type, provided with an inlet receiving signal LV, and therefrom three outlets connected to three memory-registers, 931, 941 and 951, and a control inlet connected to the outlet of a meter, 921.

Meter 921 is of a known type that computes, modulo 3, displacements to higher level of binary signal H, which it receives on its counting inlet. Thus, if multiplexer 911 is in the state where the inlet receiving signal LV is connected to the memory-register 931, a displacement to the higher level of signal H controls a change of state of multiplexer 911 to connect the inlet receiving signal LV to the memory-register 941, and so on.

Each memory-register 931, 941 and 951, of known type, is provided with a writing control inlet receiving signal S1, a zero point correction (clear) control inlet receiving signal NR, and an outlet. The three outlets of memory-registers 931, 941 and 951 are connected to the three inlets of a summator 961, whose outlet delivers a digital signal LV'.

An adder 971 is provided with a first inlet receiving signal LV', a second inlet receiving the outlet signal LV" of a memory-register, 981, and an outlet, connected to the inlet of memory-register 981, and delivering signal LVC.

The memory-register, 981, of known type, is provided with a writing control inlet receiving signal VR and a zero point correction control inlet receiving signal JS.

The processing path for signal FR is deduced from the above by replacing, in each reference numeral, the units number, worth 1, by number 2. Thus signal S2 is received by the writing control inlet of memory-registers 932, 942 and 952.

The same applies to the other paths.

Circuit 9, for composing and monitoring meals, also includes a computing circuit 195, provided with nine inlets receiving signals LV', FR', . . . ALC' and an outlet delivering a digital signal, CAS'. The computing circuit, 195, is identical with the computing circuit, 24, already described.

A computing circuit, 197, provided with an inlet receiving signal CASA, and an outlet, is arranged to multiply said signal by a fraction which is less than 1, here worth 7/10.

A digital comparator, 196, of known type, provided with a first inlet receiving signal CAS', a second inlet receiving the circuit outlet signal, 197, and a binary outlet connected to an indicator light, 198, controls here the switching of the light if the signal which is applied on its first inlet is above the signal which is applied on its second inlet.

An electronic circuit, 193, is provided with nine inlets receiving signals LV', FR', ... ALC', and a binary outlet connected to an indicator light 194. Electronic circuit 193 is here arranged to detect the following signal combination: LV'=FR'=VP'=LA'=FM'=0 FC', BH', SU', ALC' indifferent and to control switching of light 194. Detector circuit 193 is within reach of any specialist and will not be further described.

A counter, 191, of known type, is provided with a counting inlet receiving signal VR, a zero point correction control inlet receiving signal JS and an outlet delivering a digital signal representing the number of displacements to the higher level of signal VR.

A comparing circuit, 192, is provided with an inlet connected to the outlet of counter 191, and two binary outlets each connected to an indicator light, 199. The comparing circuit, 192, is arranged to compare the numerical value at its entrance to the terminals of a number range, in this case range 3, 4, 5 and 6, and to control one of the indicator lights, 199, if that number is less than 3, and the other indicator light if that number is more than 6. Circuit 192 is within the reach of any specialist and will not be further described.

Figure 3:
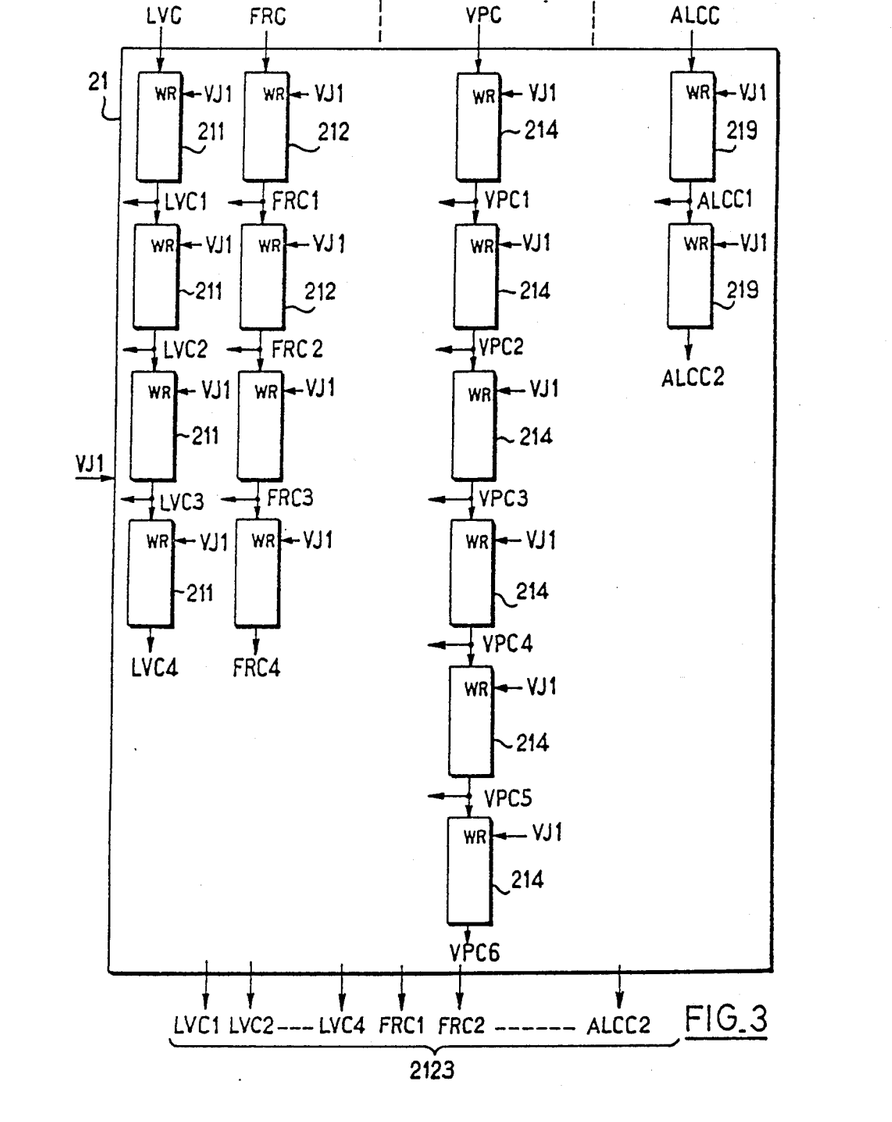
FIG. 3 is a structure diagram of the memorizing circuit for quantities consumed during preceding days, which circuit is a part of the device of FIG. 1.

The arrangement of circuit 21, for memorizing amounts consumed during preceding days, is now described by reference to FIG. 3.

The memory circuit, 21, is here arranged in nine chains of memory-registers, 211-219, of known type, cascade mounted within a chain.

Memory-registers are all provided with a writing control inlet receiving binary signal VJ1.

Each chain of registers, 211-219, follows one of the nine inlets, LVC, FRC, ... ALCC. The number of registers in a chain depends upon the inlet it follows. As an example, Table III gives the number of registers in each chain.

TABLE III

| Chain | Registers' reference numerals | Number of registers |
|---|---|---|
| LVC | 211 | 4 |
| FRC | 212 | 4 |
| FCC | 213 | 4 |
| VPC | 214 | 6 |
| LAC | 215 | 6 |
| FMC | 216 | 6 |
| BHC | 217 | 2 |
| SUC | 218 | 2 |
| ALCC | 219 | 2 |

The outlet of each register, 211-219, is connected to bundle 2123. The outlet of a chain's register delivers a digital signal to which is given the name of the chain's signal followed by the register's rank in the chain. Thus the third register, 214, delivers signal VPS3. In FIG. 3, only chains LVC, FRC, VPC and ALCC are represented, so as not to blur the drawing.

Figure 4:
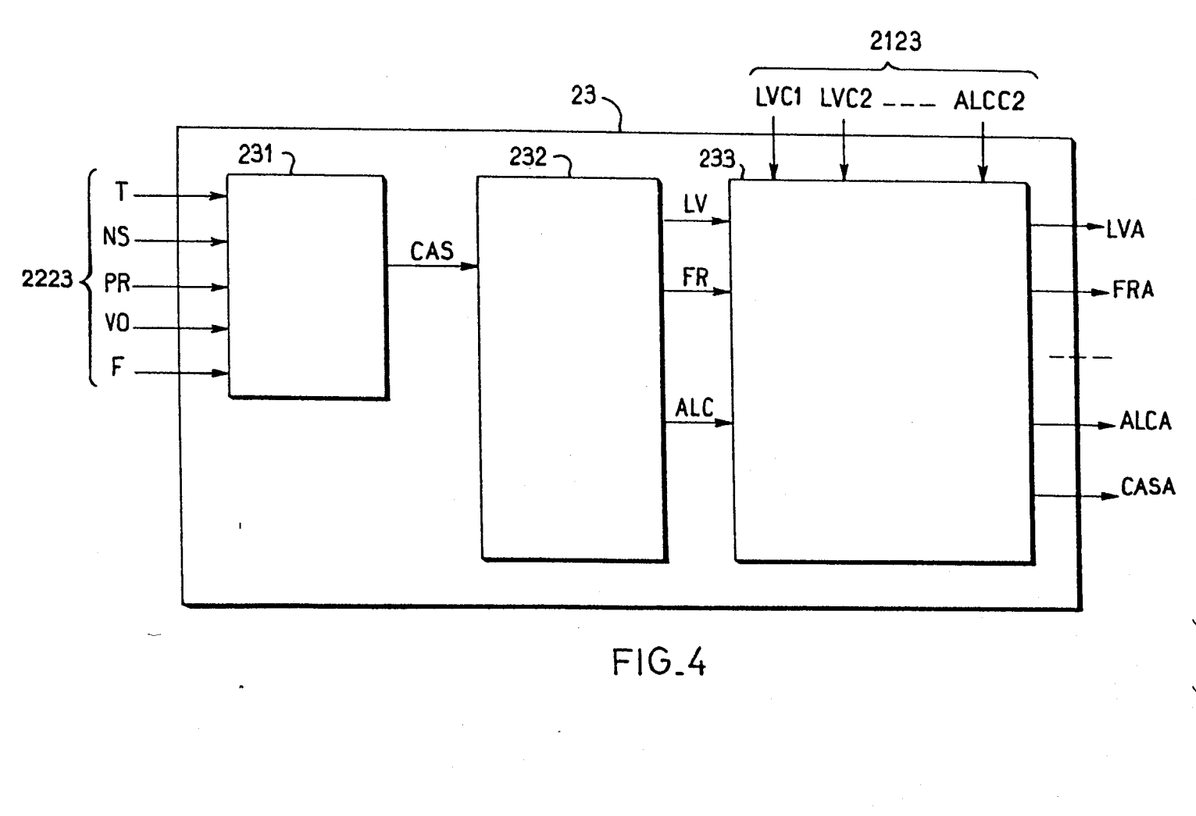
FIG. 4 is a block diagram of the circuit for computing recommended quantities for the day, which circuit is a part of the device of FIG. 1.

The computing circuit, 23, is now described referring to FIG. 4.

A computing circuit, 231, of the daily energy ration suited to the case is provided with a plurality of inlets receiving bundle 2223, and an outlet delivering signal CAS. Circuit 231 completes a number of simple operations on the digital signals it receives. Thus, as an example, if these signals are signals T, NS, PR, UO and F, circuit 231 completes the following computations.

Ideal weight PID is first calculated:

$$PID = VO\,[T - 100 - (T - 150)/NS]$$

then the ideal daily energy ration CAI:

$$CAI = 2000 + 25\,(PID - 50) + 500\,(P - 1)$$

then the weight difference DP:

$$DP = 100\,(PR - PID)/PID$$

then coefficient QN between the daily energy ration suited to the case and the ideal daily energy ration:

$$QN = 1 - 2\,DP/100$$

(with lower limit 0.6 and higher limit 1) and finally the daily energy ration CAS suited to the case:

$$CAS = CAI \times QN$$

(with lower limit 1200 cal.)

The computing circuit, 231, is thus within reach of any specialist and will not be further described.

A circuit, 232, for computing daily quantities of food in each category suited to the case is provided with an inlet receiving signal CAS and nine outlets delivering digital signals LV, FR, ... ALC. Circuit 232 computes functions of the digital signal CAS it receives.

As a first example, circuit 232 completes here the following calculations (system of quadratic equations):

$$LV = 0.1.CAS + 400$$

$$FR = 0.15.CAS + 80$$

$$FC = 0.13.CAS - 150$$

$$VP = 0.06.CAS + 220$$

$$LA = 0.024.CAS + 250$$

$$FM = 0.02.CAS + 20$$

$$BH = 0.03.CAS - 30$$

$$SU = 0.02.CAS - 25$$

$$ALC = 0.1.CAS - 100$$

The computing circuit, 232, is thus within reach of any specialist and will not be further described.

As a second example, circuit 232 can complete the following computations (system of quadratic and first degree equations):

$$LV = -0.0000090 \cdot CAS \cdot CAS + 0.135 \cdot CAS + 250$$

-continued $$FR = -0.0000060 \cdot CAS \cdot CAS - 0.090 \cdot CAS + 165$$

$$FC = -0.0000091 \cdot CAS \cdot CAS + 0.200 \cdot CAS - 175$$

$$VP = +0.060 \cdot CAS + 220$$

$$LA = +0.0000075 \cdot CAS \cdot CAS - 0.015 \cdot CAS + 140$$

$$FM = +0.0000025 \cdot CAS \cdot CAS - 0.005 \cdot CAS + 50$$

$$BH = -0.0000020 \cdot CAS \cdot CAS + 0.033 \cdot CAS - 40$$

$$SU = +0.0000080 \cdot CAS \cdot CAS - 0.012 \cdot CAS + 15$$

$$ALC = +0.100 \cdot CAS - 100$$

A circuit, 233, for computing recommended quantities and the recommended energy ration is provided with nine inlets receiving signals LV, FR, ... ALC, a plurality of inlets connected to bundle 2123, and ten outlets delivering signals LVA, FRA, ... ALCA and CASA. Circuit 233 completes simple operations on the digital signals it receives. As an example, circuit 233 completes here the following calculations:

$$LVA = 2LV - (LVC1 + LVC2 + LVC3 + LVC4)/4$$

$$FRA = 2FR - (FRC1 + FRC2 + FRC3 + FRC4)/4$$

$$FCA = 2FC - (FCC1 + FCC2 + FCC3 + FCC4)/4$$

$$VPA = 2VP - (VPC1 + VPC2 + VPC3 + VPC4 + VPC5 + VPC6)/6$$

$$LAA = 2LA - (LAC1 + LAC2 + LAC3 + LAC4 + LAC5 + LAC6)/6$$

$$FMA = 2FM - (FMC1 + FMC2 + FMC3 + FMC4 + FMC5 + FMC6)/6$$

$$BHA = 2BH - (BHC1 + BHC2)/2$$

$$SUA = 2SU - (SUC1 + SUC2)/2$$

$$ALCA = 2ALC - (ALCC1 + ALCC2)/2$$

$$CASA = 0.4LVA + 0.5FRA + 3FCA + 1.6VPA + 0.8LAA + 2.5FMA + 6BHA + 4SUA + 0.7ALCA$$

The computing circuit, 233, is thus within reach of any specialist and will not be further described.

The device which is just described works as follows.

The user begins at first by entering his morphological data into memory 22, in a conventional, therefore not described, manner, for instance with the keys of a keyboard.

Circuit 231 then computes the daily energy ration CAS adapted to these morphological data.

Circuit 232 then computes, from the daily energy ration CAS, daily amounts of food LV, FR, ... ALC, suited to these morphological data, in each food category.

Later, when the device is started for the first time, is scheduled an initialization procedure for memory 21, completed by way of known means, and not represented in the figures for the sake of simplicity. During this initialization procedure, the amount LV is inscribed in all 211 registers, the amount FR in all 212 registers, and so on. As will be more clearly apparent later, this amounts to supposing that the user has followed an ideal diet during the days preceding the device's first starting.

The device is then ready for daily use, which will only become totally efficient after about a week, when the amount of food really absorbed by the user during this period will have been taken into account.

Before composing the first course of the first day's first meal the user operates switch 92 and switch 93, signals NR and H move to the higher level, registers 931-939, 941-949 and 951-959 are set to zero and multiplexers 911-919 are in such a state that their inlet is connected to registers 931-939, respectively.

The user then puts down on the scale's pan, 7, one food category after another, the varied amounts making up the first meal's first course.

When weighing green vegetables, the user operates switch S1, which as a result writes down in register 931 the weight, representative of the amount of green vegetables anticipated for the first course. When weighing fruit, he/she operates S2, which writes down in register 932 (not represented in the drawings) the amount of fruit anticipated, and so on until the amount of alcohol is written down in register 939.

To pass on to the composition of the second course, the user operates switch 93, which displaces signal H to the higher level and controls the connection between the inlet of multiplexers 911-919 and registers 941-949, respectively. The food is weighted as for the first course, and the amounts are then written down in registers 941-949.

The composition of the third course proceeds in the same manner, it being understood that the limit has been set to three courses in this description only to avoid making it overly complicated.

Thus it can be said that switches 92, 93, 81-89, counters 921-929, multiplexers 911-919 and registers 931-939, 941-949 and 951-959 allow to memorize each anticipated amount, per course in the meal, of food from each category.

The computing circuit, 195, then computes signal CAS' which is representative of the meal's energy value. If this value is above seven-tenths of CASA, CASA representing, as will be seen more clearly later, the daily recommended energy ration, this switches on light 198, indicating that the meal is too copious.

If the detecting circuit, 193, detects a simultaneous absence of food from categories LV, FR, VP, LA and FM, light 194 is switched on, indicating an imbalance in the meal.

It can thus be said that the detecting circuit, 193, the computing circuits, 195 and 197, and comparator 196 monitor the meal's composition.

If none of the lights, 194 and 198, is switched on, the user as a rule validates his/her meal by operating switch 91. If one of the lights, 194 and 198, is switched on, the user can revise the composition of his/her meal if he/she wants to, so as to make it less copious, or better balanced, or both. But he/she can also disregard this indication and validate this ill-composed meal, if he/she decides to eat it, by operating switch 91.

The operation of switch 91 entails activation of signal VR and therefore writing down, in registers 981-989, of values LV"=LV', FR"=FR', ... ALC"=ALC' because the outlet of registers 981-989 was initially at zero point.

When the user wants to prepare his/her second meal of the day, he/she operates switch 92, which entails zero point correction of registers 931-939, 941-949 and 951-959.

The composition stages for the second meal are naturally the same as those for composing the first meal.

When the user decides to validate his second meal, he operates switch 91, which entails writing down, in registers 981-989, of the values of signals LV", FR", ... ALC" which are now representative of the amounts of food consumed during the first two meals, whereas the value of signals LV', FR', ... ALC' represent the amounts consumed during the second meal.

The user proceeds in the same manner for the following meals. Signals LV", FR", ... ALC" are thus representative of the amounts consumed during the whole of past meals of said day.

Switch 91, adders 971-979 and registers 981-989 operate to memorize signals LV", FR", ... ALC" representative of these amounts.

Having anticipated the composition of his/her last meal in the day, and before validating this meal, indicators 50-59 tell the user the difference between the amounts anticipated for the day, LVC, FRC, ... ALCC, respectively, and the recommended amounts, LVA, FRA, ... ALCA, respectively, computed as will be seen later.

The user can either modify the composition of his last meal, to end up with amounts anticipated in agreement with recommended amounts, or disregard this indication and validate the last meal, by operating switch 91, and then validate the day, by operating switch 60.

Likewise, at day's end, lights 199 tell the user whether he has had too few meals, that is to say here less than 3, or on the contrary too many, that is to say here more than 6.

As signal VJ1 is activated by circuit 6, the amounts LVC, FRC, ... ALCC, then representing the amounts consumed during the day, are written down in the first registers 211-219, the content of the first registers then passing into the second registers, and so on, the content of end-of-chain registers being lost.

Thus the amounts LVC1, FRC1, ... ALC1 represent the amounts consumed during the day, the amounts LVC2, FRC2, ... ALC2 those consumed during the preceding day, and so on ...

The computing circuit, 233, then determines recommended amounts for the day to come, LVA, FRA, ... ALCA, and the recommended caloric ration CASA with the help of formulae already given as exemplary. It will be noted that in these formulae past days' consumptions are not identically taken into account for all types of food.

Thus the nine food categories are here subdivided into three groups, according to their daily essentialness. The first group comprises categories VP, LA and FM including food that can be considered as almost daily indispensable, the second group comprises categories LV, FR and FC, whose indispensable amount tolerates wide variations, and the third group comprises categories BH, SU and ALC, of which one can be deprived during long intervals, if not permanently, without any real damage to the health.

Computation circuit 233 determines recommended amounts for the day to come as a function of the amounts consumed on the preceding days, these days being taken in all the greater number that this food presents a daily indispensable character.

Thus consumption of first group food is here averaged on seven days, that of second group food, on five days, and that of third group food, on three days.

Each recommended amount is that which would equate consumption on the averaging period to that which is adapted to the morphological data.

The recommended amounts, LVA, FRA, ... ALCA, and the recommended energy ration CASA, as determined by circuits 22 and 23, are written down in registers 31-39, and 30, respectively, during activation of signal VJ2 by circuit 6.

The device is then ready for another day, which the user starts by operating switch 94, so as to activate signal JS to correct counter 191 and registers 981-989 to zero point.

The inventive device can naturally be embodied with discrete electronic components, but also with a microprocessor and its associated circuits.

Naturally this invention is not limited to the above description.

Specifically, computations made by circuits 231, 232 and 233 make use of formulae which are used in dietetics. These formulae may well be changed without questioning the inventive device, for instance as a function of the applied dietetic principles, or the particular diet to which the user can be subjected.

Likewise, the substraction circuits, 40-49, which in fact are used for comparing the anticipated amounts, LVC, FRC, ... ALCC, to the recommended amounts, LVA, FRA, ... ALCA, and the anticipated energy ration, CASC, to the recommended energy ration, CASA, could be replaced by plain comparators, and the display devices, 50-51, could be replaced by plain indicator lights.

It is also within reach of a specialist to anticipate the possibility of taking into account a given course, for instance a ready-made course, not from the weight of its components, but from the proportions of its varied components, as a reference to the food categories available on the device.

Naturally, the inventive device being an electronic device it can be endowed with certain improvements within reach of a specialist, so as to make it more pleasant in use, as for instance:

a clock showing day and hour the ability to compare, at any moment, anticipated to adapted amounts of food, total or partial zero point correction of the memory circuit for amounts consumed on the preceding days, the ability to program the device at will according to other nutritional theories than that expressed by the algorithm contained in the apparatus, by way of programming keys or external elements such as memory cards, PROMS or other memory means.

Figure 5:
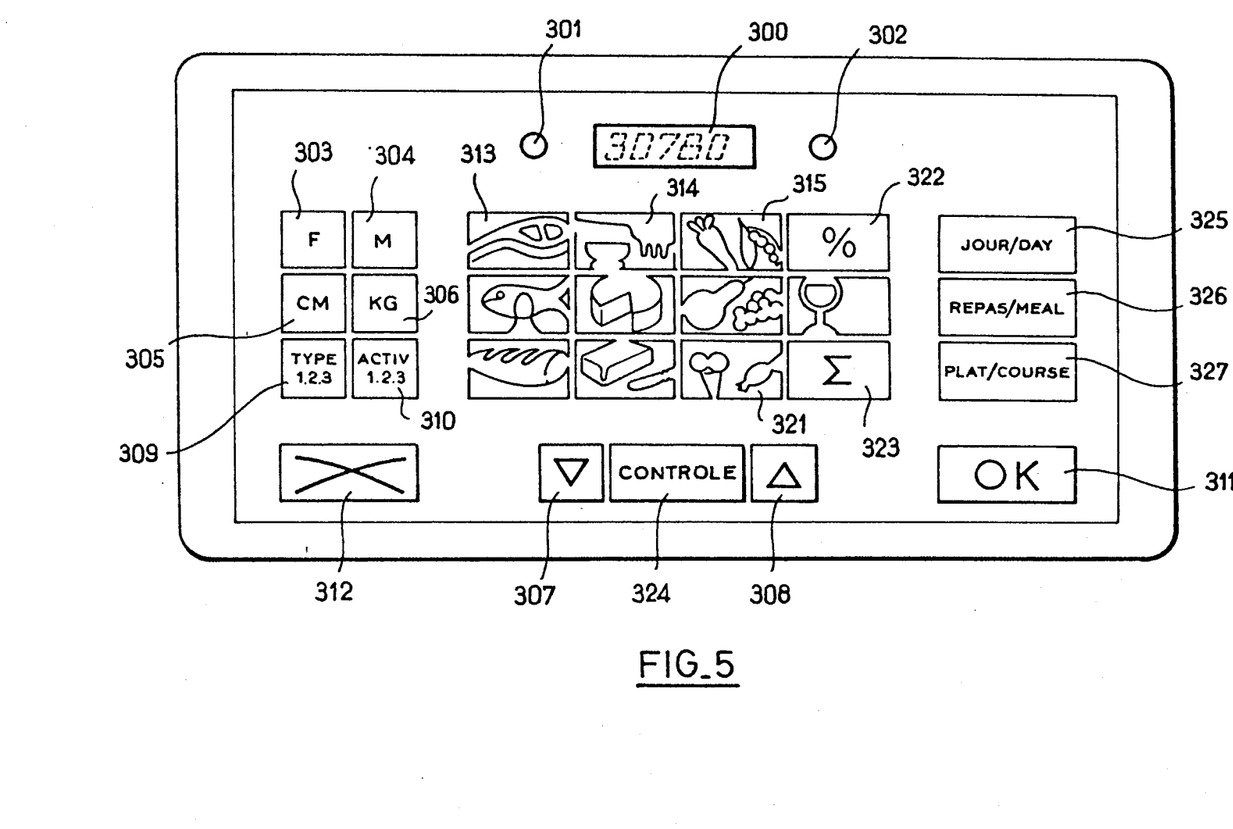
FIG. 5 is a keyboard diagram of an inventive device.

The invention also contemplates an embodiment without associated scales, in the form of a small size device whose keyboard and front side are shown on FIG. 5. In this embodiment, the front side of the housing containing the above-described electronic elements comprises a display means, 300, for instance LCD type, flanked by two lights, 301 and 302, respectively red and green. Keys 303 and 304 allow the user to select sex, keys 305 and 306 to display his/her height and weight by operating control keys, 307 and 308, also used for entering user's morphology and activity characteristics marked out with keys 309 and 310.

Key 311, labelled OK, validates entries made, and key 312 is provided for cancelling.

Food categories are diagrammatically represented on nine keys, 313-321; key 322 is labelled '%', key 323 is labelled 'Σ', key 324 is labelled 'monitoring', and three keys, 325–327, are labelled 'DAY', 'MEAL', 'COURSE', respectively.

After operating on-off switch the user's characteristics as entered with keys 303–310 are validated by pressing key 311.

Likewise, food categories are entered with keys 313–321, key 322 being used for entering foods whose energy value differs from that category's average value, by referring to an equivalence table and operating keys 307 and 308.

When all is entered, pressing key 311 validates the procedure. If one presses this key together with key 327, the course is validated, or the meal if one uses key 326, or the day if one presses the key labelled 325.

To enter a complex course one presses first key 323, 'Σ', then pressing keys 307 and 308 allows display of the course's total weight, key 322 is then pressed, then another key, 313–321, and again keys 307 and 308 in order to adjust the percentage of the total weight represented by a first ingredient, then validating key 311, then another key 313–321, &c ... till final validation through pressing of keys 311 and 323 or 311 and 327.

In order to monitor the state of the authorized ration, pressing key 324 and one of keys 313–321 produces display of the amount, in grams, still admitted for that day in the food category corresponding to pressed key. Simultaneously, switching on light indicates that the entire authorized ration has been consumed if the light is permanent, whereas a flickering light indicates less than 25% of authorized ration is left. Conversely, permanent lighting of light 302 reveals there is only 25% of authorized ration left and a flickering light reveals a deficiency.

For monitoring the global situation, one presses keys 324 and 323: this triggers lighting of light 301 if one of the rations is totally consumed or lighting of light 302 in case an element is deficient.

We claim:

1. A device for implementing a method for feeding persons in which, food being subdivided in a given number of categories according to energy values, the recommended energy ration for a given day to a given person depends upon the energy rations consumed by said person during the preceding days, which device comprises in combination:
   - a first memory means (11–19, 81–89) to memorize each quantity (LVC, FRC, ... ALCC), as anticipated by said person, of food belonging to each of said categories for his/her diet during that day,
   - a second memory means (21) connected to the outlet of said first memory means (11–19) to memorize each quantity (LVC1, LVC2, ..., LVC4, FRC1, FRC2, ... ALCC2), as consumed by said person, of food belonging to each of said categories during at least one of said preceding days,
   - a first computer means (22, 23), connected to the outlet of said second memory means (21), to determine each quantity (LVA, FRA, ... ALCA) of food in each of said categories which is recommended for said person based on the quantities consumed on preceding days, as well as said energy ration (CASA), recommended to said person, for his/her diet during said day,
   - a third memory means (30–39), connected to the outlet of said first computer means (22, 23), to memorize said recommended quantities (LVA, FRA, ... ALCA) and said recommended energy ration (CASA),
   - a second computer means (24), connected to the outlet of said first memory means (11–19) to determine the energy ration (CASC), as anticipated by said person, for his/her diet during said day,
   - a first comparison means (40–49) connected to the outlet of said first memory means (11–19), to the outlet of said second computer means (24) and to the outlet of said third memory means (30–39), to compare each of said anticipated quantities (LVC, FRC, ... ALCC) to each said recommended quantity (LVA, FRA, ... ALCA) in the same category, and to compare said anticipated energy ration (CASC) to said recommended energy ration (CAS),
   - a first indicator means (50–59), controlled by the outlet of said first comparison means (40–49), and
   - controlling means (6, 60) for writing, in said second memory means (21), said anticipated and consumed quantities (LVC, FRC, ..., ALCC) and then writing, in said third memory means (30–39), new recommended quantities of food in each of said categories, and the new recommended energy ration for the next day.

2. A device according to claim 1, including moreover,
   - a fourth memory means (911–919, 921–929, 931–939, 941–949, 951–959, 93, 81–89, 92) to memorize each anticipated quantity, per course in a meal, of food from each of said categories,
   - a summing up means (961–969), connected to the outlet of said fourth memory means (931–939, 941–949, 951–959) to sum up said anticipated quantities, per course, of food from the same category, and thus deliver anticipated quantities (LV', FR', ... ALC'), for said meal, of food from each of said categories, and
   - a fifth memory means (971–979, 981–989, 91) connected to the outlet of said summing up means (961–969) to memorize each consumed quantity (LV'', FR'', ... ALC'') during all past meals of said day, of food from each of said categories, and connected to the inlet of said first memory means (11–19).

3. A device according to claim 2, including moreover:
   - a monitoring means (193, 195–197) connected to the outlet of said summing up means (961–969) and to the outlet of said third memory means (30), to monitor the composition of a meal, and
   - a second indicator means (194, 198), controlled by said monitoring means (193, 195–197).

4. A device according to claim 3, in which said monitoring means include:
   - a third computing means (195), connected to the outlet of said summing up means (961–969), to determine the energy value (CAS') of a meal,
   - a fourth computing means (197), connected to the outlet of said third memory means (30) to determine a given fraction of said recommended energy ration (CASA),
   - a second comparison means (196) connected to the outlet of said third computing means (195) and to the outlet of said fourth computing means (197) for comparing said energy value (CAS') with said fraction and controlling said second indicator means (198) when said energy value (CAS') is superior to said fraction.

5. A device according to claim 3, in which said monitoring means include means (193), connected to the outlet of said summing up means (961-969), for detecting the absence of food from given categories and for controlling said second indicator means (194) in case of detection.

6. A device according to claim 1, further including:
   computing means (91, 191) to determine the number of meals during a day,
   a third comparison means (192), connected to the outlet of said computing means (91, 191) to compare said number of meals to the limits of a given number interval, and
   a third indicator means (199), connected to the outlet of said second comparison means (192), controlled when said number of meals is inferior to said number interval.

7. A device according to claim 1, in which said first computing means include:
   a sixth memory means (22) for storing said person's morphological data (T, NS, PR, UO, F),
   a fifth computing means (231), connected to the outlet of said sixth memory means (22), to determine the daily energy ration (CAS) adapted to said morphological data (T, NS, PR, UO, F),
   a sixth computing means (232), connected to the outlet of said fifth computing means (231), to determine each daily quantity (LV, FR, . . . ALC), adapted to said morphological data (T, NS, PR, UO, F), of food to be consumed in each category,
   a seventh computing means (233), connected to the outlet of said sixth computer means (232), and to the outlet of said second memory means (21) to determine each said recommended quantity (LVA, FRA, . . . ALCA) and said recommended energy ration (CASA).

8. A device according to claim 7, in which said seventh computing means (233) are arranged so as to determine each said recommended quantity (LVA, FRA, . . . ALCA) of food from each of said categories as a function, on the one hand, of said adapted daily quantity (LV, FR, . . . ALC) of this food, and on the other hand, of the quantity (LVC1+LVC2+LVC3+LVC4, FRC1+FRC2, . . . ALC1+ALC2) of this food consumed during said preceding days.

9. A device according to claim 7, in which said sixth computing means (232) are arranged so as to determine each said adapted daily quantity (LV, FR, . . . ALC), from said adapted daily energy ration (CAS).

10. A device according to claim 1, including moreover:
    a food scale (7), delivering a signal (E) representative of the weigh of the quantity of food weighted, and
    a multiplexing means (8, 81-89), connected to the outlet of said scale (7) and to the inlet of said first memory means (11, 19).

11. A device according to claim 1, further comprising a housing containing the constituent elements of the memory means, the computing means, the comparison means, and the controlling means, and said housing has on one of its sides a keyboard for entering data and display means for displaying entered data and stored information.

* * * * *